(12) United States Patent
Park et al.

(10) Patent No.: US 10,159,417 B2
(45) Date of Patent: Dec. 25, 2018

(54) APPARATUS AND METHOD FOR MEASURING PULSE WAVE

(71) Applicant: SAMSUNG ELECTRONICS CO., LTD., Suwon-si (KR)

(72) Inventors: Sangyun Park, Hwaseong-si (KR); Jaemin Kang, Seoul (KR); Younho Kim, Hwaseong-si (KR); Yongjoo Kwon, Yongin-si (KR); Sunkwon Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 240 days.

(21) Appl. No.: 14/798,572

(22) Filed: Jul. 14, 2015

(65) Prior Publication Data

US 2016/0150985 A1     Jun. 2, 2016

(30) Foreign Application Priority Data

Dec. 2, 2014   (KR) .................... 10-2014-0170830

(51) Int. Cl.
*A61B 5/021* (2006.01)
*A61B 5/0285* (2006.01)
*A61B 5/024* (2006.01)
*A61B 5/02* (2006.01)
*A61B 5/00* (2006.01)

(52) U.S. Cl.
CPC ...... *A61B 5/02416* (2013.01); *A61B 5/02007* (2013.01); *A61B 5/02125* (2013.01); *A61B 5/7242* (2013.01)

(58) Field of Classification Search
CPC .......... A61B 5/021258; A61B 5/02108; A61B 5/0285
See application file for complete search history.

(56) References Cited

U.S. PATENT DOCUMENTS

| 3,774,593 | A | * | 11/1973 | Hakata | ................. | A61B 5/0476 600/544 |
| 3,910,258 | A | * | 10/1975 | Pisarski | ............... | A61B 5/0476 600/544 |
| 4,354,505 | A | * | 10/1982 | Shiga | .................. | A61B 5/0482 128/905 |
| 4,954,786 | A | * | 9/1990 | Yamakawa | ............... | H01S 5/50 250/205 |

(Continued)

FOREIGN PATENT DOCUMENTS

| EP | 0443267 | * | 8/1991 | .......... A61B 5/0285 |
| JP | 2003-244780 A | | 8/2003 | |

(Continued)

*Primary Examiner* — William Levicky
(74) *Attorney, Agent, or Firm* — Sughrue Mion, PLLC

(57) ABSTRACT

There are provided an apparatus and a method for measuring pulse waves. The pulse wave measuring apparatus includes a receiver configured to receive pulse wave signals sensed at at least two points of an object; an analog signal processor configured to amplify a voltage difference between two pulse wave signals from among the received pulse wave signals and integrate the amplified voltage difference; and a digital signal processor configured to analog to digital convert a value of the integrated amplified voltage difference and obtain, from the converted value, a pulse transit time between the two points corresponding to the two pulse wave signals.

18 Claims, 13 Drawing Sheets

(56) References Cited

U.S. PATENT DOCUMENTS

| | | | |
|---|---|---|---|
| 5,255,686 A | 10/1993 | Takeda et al. | |
| 5,873,834 A * | 2/1999 | Yanagi | A61B 5/02125 600/485 |
| 6,208,286 B1 * | 3/2001 | Rostislavovich | A61B 5/0507 342/118 |
| 7,674,231 B2 * | 3/2010 | McCombie | A61B 5/02125 600/481 |
| 7,678,048 B1 * | 3/2010 | Urbano | A61B 8/00 367/103 |
| 8,773,107 B2 * | 7/2014 | Jackson | G01R 29/0814 324/228 |
| 2013/0310677 A1 | 11/2013 | Chiu | |
| 2014/0236031 A1 * | 8/2014 | Banet | A61B 5/6831 600/513 |
| 2014/0297218 A1 * | 10/2014 | Yuen | A61B 5/02438 702/141 |
| 2015/0112606 A1 * | 4/2015 | He | A61B 5/029 702/19 |
| 2016/0015282 A1 * | 1/2016 | Kim | A61B 5/02108 600/480 |
| 2016/0022145 A1 * | 1/2016 | Mostov | A61B 5/0004 340/870.07 |
| 2017/0281024 A1 * | 10/2017 | Narasimhan | A61B 5/02125 |

FOREIGN PATENT DOCUMENTS

| | | |
|---|---|---|
| KR | 10-2004-006602 A | 7/2004 |
| KR | 10-1068116 B1 | 9/2011 |

* cited by examiner

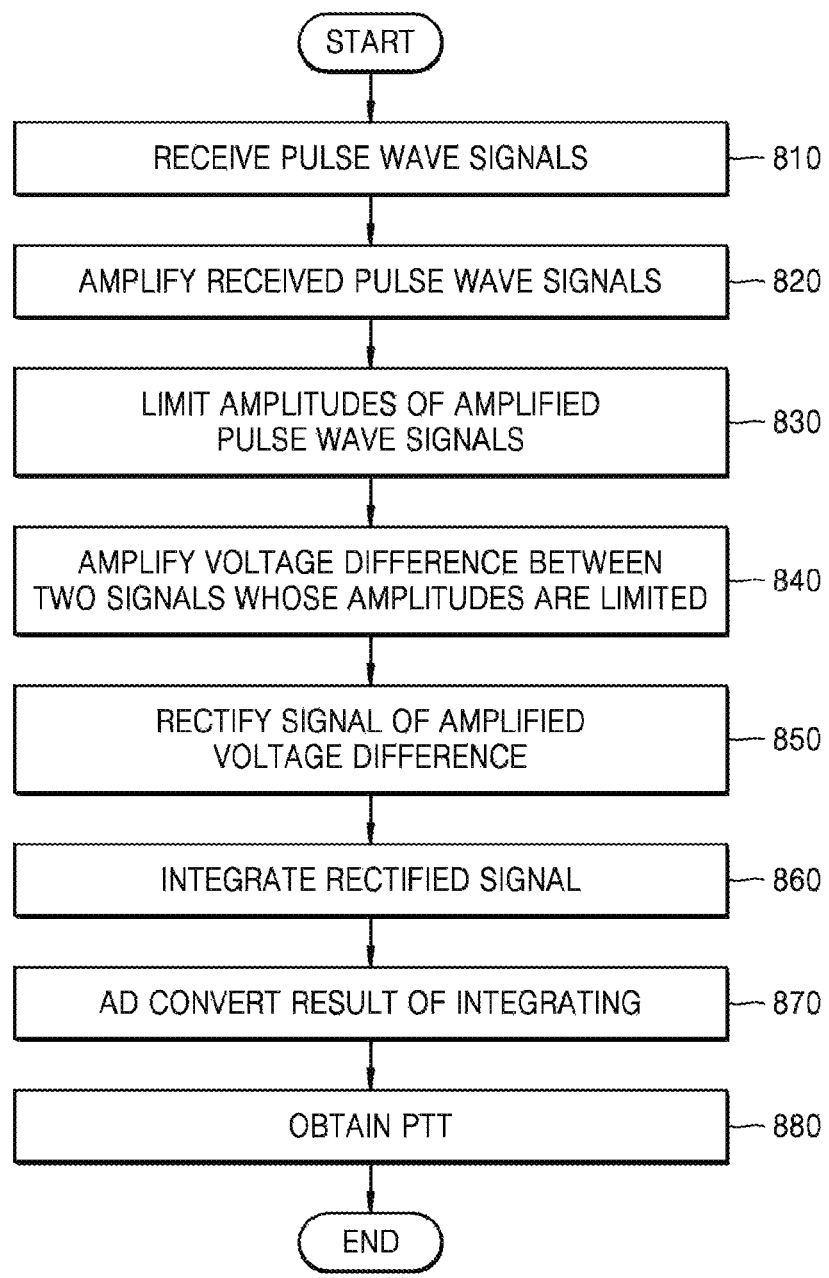

APPARATUS AND METHOD FOR MEASURING PULSE WAVE

CROSS-REFERENCE TO RELATED APPLICATION

This application claims priority from Korean Patent Application No. 10-2014-0170830, filed on Dec. 2, 2014 in the Korean Intellectual Property Office, the disclosure of which is incorporated herein in its entirety by reference.

BACKGROUND

1. Field

Apparatuses and methods consistent with exemplary embodiments relate to measuring a pulse wave that carries biological information.

2. Description of the Related Art

In a commonly used pulse transit time (PTT) measuring method, PTT is obtained by measuring an electrocardiogram signal and comparing the measured electrocardiogram signal with a pulse wave measured at an extremity of a body, such as a hand or a foot which is the farthest point from the heart. When the electrocardiogram signal is used, a potential difference must be measured through an electrical path including the heart, and therefore a device must be in contact with both hands or a patch must be attached to the chest.

In a method of measuring the pulse wave without measuring the electrocardiogram signal, pulse waves are measured at two points of the extremity of the body and a time difference between a pulse wave signal at the point closer to the heart and a pulse wave signal at the point closer to the end of the body is measured. At this time, the smaller a distance between the two points at which the pulse wave signals are sensed, the smaller the time difference between the two pulse wave signals. Therefore, the smaller the distance between the two points at which the pulse wave signals are sensed, the higher a sampling frequency required for measuring the pulse wave signals.

SUMMARY

One or more exemplary embodiments provide an apparatus and a method for obtaining pulse transit time (PTT) between two points of an object by integrating a result of differentially amplifying pulse wave signals sensed at the two points of the object and analog to digital (AD) converting the result of the integrating.

According to an aspect of an exemplary embodiment, there is provided a pulse wave measuring apparatus including: a receiver configured to receive pulse wave signals sensed at at least two points of an object; an analog signal processor configured to amplify a voltage difference between two pulse wave signals from among the received pulse wave signals and integrate the amplified voltage difference; and a digital signal processor configured to analog to digital (AD) convert a value of the integrated amplified voltage difference and obtain, from the converted value, a pulse transit time (PTT) between the two points corresponding to the two pulse wave signals.

The analog signal processor may include: a differential amplifier configured to amplify the voltage difference between the two pulse wave signals; and an integrator configured to integrate a signal of the amplified voltage difference.

The analog signal processor may include a rectifier configured to rectify a signal of the amplified voltage difference.

The rectifier may be further configured to perform full-wave rectification on the signal of the amplified voltage difference.

The rectifier may be further configured to perform half-wave rectification on the signal of the amplified voltage difference.

The analog signal processor may further include an amplifier configured to amplify the received pulse wave signals.

The analog signal processor may further include an amplitude limiter configured to limit amplitudes of the amplified pulse wave signals to a predetermined value in response to the amplitudes of the amplified pulse wave signals being equal to or greater than the predetermined value.

The digital signal processor may be further configured to determine a point of time at which the integrated amplified voltage difference is AD converted by using one of the sensed pulse wave signals, AD convert the integrated amplified voltage difference at every determined point of time, and obtain the PTT.

The digital signal processor may further include a peak detector configured to detect a peak of one of the sensed pulse wave signals, AD convert the integrated amplified voltage difference at every determined point of time corresponding to a point of time at which the peak is detected, and obtain the PTT.

The digital signal processor may be further configured to determine a point of time at which the integrator is reset by using one of the sensed pulse wave signals, and wherein the integrator may be reset at every determined point of time.

The pulse wave measuring apparatus may further include a light emitter configured to emit light to the object, wherein the receiver may be further configured to receive at least one of light that is emitted from the light emitter and pass through the object and light that is emitted from the light emitter and reflected from the object, photoelectrically convert the received light, and generate the pulse wave signals.

According to an aspect of another exemplary embodiment, there is provided a pulse wave measuring method including: receiving pulse wave signals sensed at at least two points of an object; amplifying a voltage difference between two pulse wave signals from among the received pulse wave signals; integrating the amplified voltage difference; analog-to-digital (AD) converting a value of the integrated amplified voltage difference; and obtaining, from the converted value, a pulse transit time (PTT) between the two points corresponding to the two pulse wave signals.

The integrating the amplified voltage difference may include rectifying a signal of the amplified voltage difference.

The rectifying the signal of the amplified voltage difference may include performing full-wave rectification on the signal of the amplified voltage difference.

The rectifying the signal of the amplified voltage difference may include performing half-wave rectification on the signal of the amplified voltage difference.

The receiving the pulse wave signals may include amplifying the received pulse wave signals.

The amplifying the received pulse wave signals may include limiting amplitudes of the amplified pulse wave signals to a predetermined value in response to the amplitudes of the amplified pulse wave signals being equal to or greater than the predetermined value.

The pulse wave measuring method may further include determining a point of time at which the value of the integrated amplified voltage difference is AD converted by using one of the sensed pulse wave signals, wherein the obtaining the PTT may include AD converting the value of the integrated amplified voltage difference corresponding to every determined point of time.

The pulse wave measuring method may further include determining a point of time at which the value of the integrated amplified voltage difference is reset by using one of the sensed pulse wave signals, wherein the integrating the amplified voltage difference comprises resetting the value of the integrated amplified voltage difference at every determined point of time.

The pulse wave measuring method may further include: emitting light to the object; receiving at least one of the light that is emitted and passes through the object and light that is emitted and reflected from the object; photoelectrically converting the received light; and generating the pulse wave signals from the photoelectrically converted light.

BRIEF DESCRIPTION OF THE DRAWINGS

The above and/or other aspects will be more apparent and more readily appreciated from the following description of exemplary embodiments, with reference to the accompanying drawings, in which:

FIG. 8 is a flowchart of a pulse wave measuring method according to another exemplary embodiment.

DETAILED DESCRIPTION

Figure 1A:
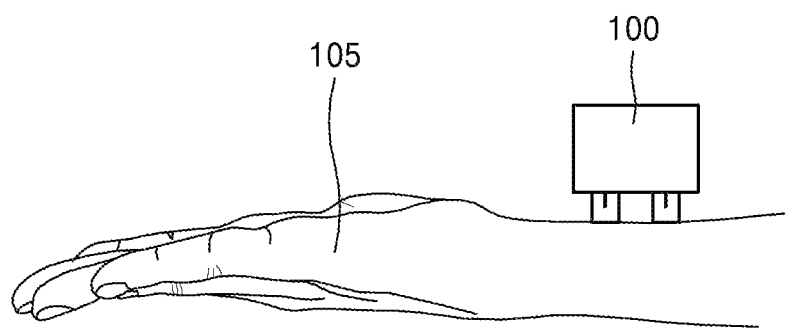
FIGS. 1A and 1B are conceptual diagram and graph of a pulse wave measuring method.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

The terms first and second, etc., are only used to distinguish one element from another element.

Unless otherwise defined, terms such as "include" and "have" are for representing that characteristics or elements described in the specification exist. It may be interpreted that one or more other characteristics or elements may be added.

It will also be understood that when an element is referred to as being "connected to" or as "contacting" another element, it can be directly connected to or can directly contact the other element. However, intervening elements may also be present. On the other hand, when an element is referred to as being "directly connected to" or as "directly contacting" another element, it can be understood that intervening elements do not exist.

Figure 1B:
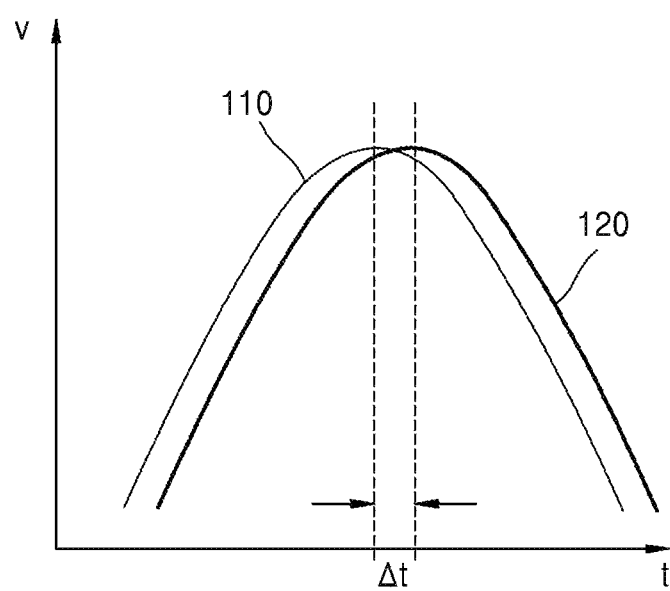

FIGS. 1A and 1B are a conceptual diagram and a graph of a pulse wave measuring method.

As shown in FIG. 1A, a pulse wave measuring apparatus 100 senses pulse waves at first and second points of an object 105 and measures transit time between a first signal 110 at the first point close to the heart and a second signal 120 at the second point close to the end of the body.

FIG. 1B illustrates waveforms of the first signal 110 and the second signal 120, and a distance Δt between peaks of the two waveforms may represent pulse transit time (PTT).

In a non-invasive pulse wave measuring method, the pulse wave measuring apparatus 100 contacts the end of the body, senses two or more body signals, and may obtain transit time between the sensed signals. The end of the body may be, for example, the wrist, the ankle, the palm, or the sole. A transit speed of pulse waves that travel through the arteries is about 1 m/s to 5 m/s. The smaller a distance between the two points at which the signals are measured, the smaller signal transit time between the two points. Accordingly, it has been known that the smaller the signal transit time between the two points, a higher sampling frequency is required for a digital system.

The pulse wave measuring apparatus 100 according to the exemplary embodiment performs analog signal processing on the pulse wave signals 110 and 120 sensed at the two points and may obtain the PTT. Specifically, the pulse wave measuring apparatus 100 integrates a result of differentially amplifying the pulse wave signals 110 and 120 sensed at the two points, analog to digital (AD) converts the result of the integrating, and may obtain the PTT. The pulse wave measuring apparatus 100 according to the current exemplary embodiment may obtain the signal transit time without being affected by the sampling frequency at which the signals are measured although the distance between the two points at which the signals are measured is small. In addition, the pulse wave measuring apparatus 100 according to the exemplary embodiment may easily obtain the signal transit time with high accuracy through amplification although magnitudes of the measured signals are very small. The measured PTT may be used for analyzing cardiovascular system characteristics such as blood pressure and elasticity of a blood vessel.

Figure 2:
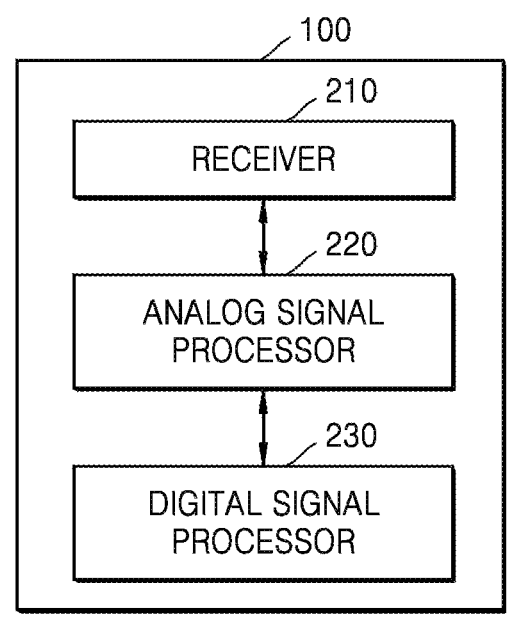
FIG. 2 is a block diagram of a pulse wave measuring apparatus according to an exemplary embodiment.

FIG. 2 is a block diagram of a pulse wave measuring apparatus 100 according to an exemplary embodiment.

As illustrated in FIG. 2, the pulse wave measuring apparatus 100 includes a receiver 210, an analog signal processor 220, and a digital signal processor 230. The pulse wave measuring apparatus 100 may be implemented by more elements than the illustrated elements.

Hereinafter, the above elements will be sequentially described.

The receiver 210 receives pulse wave signals sensed at least two points of an object.

Here, the at least two points of the object mean at least two points positioned at one end of the body of the object.

The receiver 210 may include a light receiver that receives at least one of light that is emitted from a light emitter and passes through the object and light that is reflected from the object, photoelectric converts the received light, and generates the pulse wave signals. Here, the light emitter may include at least one light emitting device that radiates the object with light. For example, the light emitter may be a visible light emitting diode (LED) or near-infrared (IR) LED. However, the present embodiment is not limited thereto.

The analog signal processor 220 amplifies a voltage difference between two pulse wave signals among the received pulse wave signals and integrates the amplified voltage difference.

The analog signal processor 220 according to the exemplary embodiment may include a differential amplifier for amplifying the voltage difference between the two pulse wave signals and an integrator for integrating a signal of the amplified voltage difference. In this case, since an output voltage of the integrator is proportional to PTT, the output voltage of the integrator may be used for obtaining the PTT.

In addition, the analog signal processor 220 may perform pre-processing for improving accuracy of measuring pulse waves with respect to the received pulse wave signals. For example, the analog signal processor 220 may perform noise filtering in order to improve signal to noise ratios (SNR) of the received pulse wave signals. In another example, the analog signal processor 220 may perform amplification for facilitating a subsequent signal processing process when magnitudes of the received pulse wave signals are small.

The analog signal processor 220 according to another exemplary embodiment may further include a rectifier for rectifying the signal of the amplified voltage difference, which will be described in detail with reference to FIGS. 3 and 4.

The analog signal processor 220 according to another exemplary embodiment may limit amplitude by amplifying the received pulse wave signals, which will be described in detail with reference to FIGS. 5 and 6.

The digital signal processor 230 AD converts the result of the integrating and obtains the PTT between the two points corresponding to the two pulse wave signals.

The digital signal processor 230 according to the exemplary embodiment receives the result of the integrating of the analog signal processor 220 at a predetermined point of time, AD converts the received result of the integrating, and may obtain the PTT. For example, the digital signal processor 230 receives the result of the integrating of the analog signal processor 220 every period smaller than a cardiac impulse period, converts the received result of the integrating to a corresponding digital signal, and obtains the PTT from the digital signal.

The digital signal processor 230 according to the exemplary embodiment may determine the point of time at which the result of the integrating is AD converted by using one of the sensed pulse wave signals. The digital signal processor 230 may receive one of the sensed pulse wave signals in order to determine the point of time at which the result of the integrating of the analog signal processor 220 is received and the received result of the integrating is AD converted. The point of time at which the result of the integrating is AD converted may be, for example, a point of time corresponding to a point of time at which a peak of one of the sensed pulse wave signals is detected, a point of time corresponding to a point of time at which a valley of one of the sensed pulse wave signals is detected, or a point of time corresponding to a point of time at which a magnitude of one of the sensed pulse wave signals is 0V. However, the present embodiment is not limited thereto.

For example, when the point of time at which the result of the integrating is AD converted is the point of time corresponding to the point of time at which the peak of one of the sensed pulse wave signals is detected, the digital signal processor 230 may include a peak detector. The point of time corresponding to the point of time at which the peak is detected may be the point of time at which the peak is detected or a point of time with a lapse of predetermined time from the point of time at which the peak is detected. However, the present embodiment is not limited thereto.

In another example, the digital signal processor 230 receives the result of the integrating from the analog signal processor 220 every point of time corresponding to the point of time corresponding to the point of time at which the magnitude of one of the sensed pulse wave signals is 0V and may AD convert the received result of the integrating. The point of time corresponding to the point of time at which the magnitude of one of the sensed pulse wave signals is 0V may be the point of time at which the magnitude of one of the sensed pulse wave signals is 0V or a point of time with a lapse of predetermined time from the point of time at which the magnitude of one of the sensed pulse wave signals is 0V. However, the present embodiment is not limited thereto.

The digital signal processor 230 according to the exemplary embodiment may determine a point of time at which the result of the integrating is reset by using one the sensed pulse wave signals. The digital signal processor 230 may receive one of the sensed pulse wave signals in order to determine the point of time at which the result of the integrating is reset. The point of time at which the result of the integrating is reset may be, for example, a point of time corresponding to a point of time at which a peak of one of the sensed pulse wave signals is detected, a point of time corresponding to a point of time at which a valley of one of the sensed pulse wave signals is detected, or a point of time corresponding to a point of time at which a magnitude of one of the sensed pulse wave signals is 0V. However, the present embodiment is not limited thereto.

For example, when the point of time at which the result of the integrating is reset is the point of time corresponding to the point of time at which the peak of one of the sensed pulse wave signals is detected, the digital signal processor 230 may include a peak detector. The point of time corresponding to the point of time at which the peak is detected may be the point of time at which the peak is detected or a point of time with a lapse of predetermined time from the point of time at which the peak is detected. However, the present embodiment is not limited thereto.

In another example, the digital signal processor 230 may reset the result of the integrating at every point of time corresponding to the point of time corresponding to the point of time at which the valley of one of the received pulse wave signals is detected. The point of time corresponding to the point of time at which the valley is detected may be the point of time at which the valley is detected or a point of time with a lapse of predetermined time from the point of time at which the valley is detected. However, the present embodiment is not limited thereto.

In another example, the digital signal processor 230 may reset the result of the integrating every point of time corresponding to the point of time at which the magnitude of one of the sensed pulse wave signals is 0V. The point of time corresponding to the point of time at which the magnitude of one of the sensed pulse wave signals is 0V may be the point of time at which the magnitude of one of the sensed pulse wave signals is 0V or a point of time with a lapse of predetermined time from the point of time at which the magnitude of one of the sensed pulse wave signals is 0V. However, the present embodiment is not limited thereto.

Figure 3:
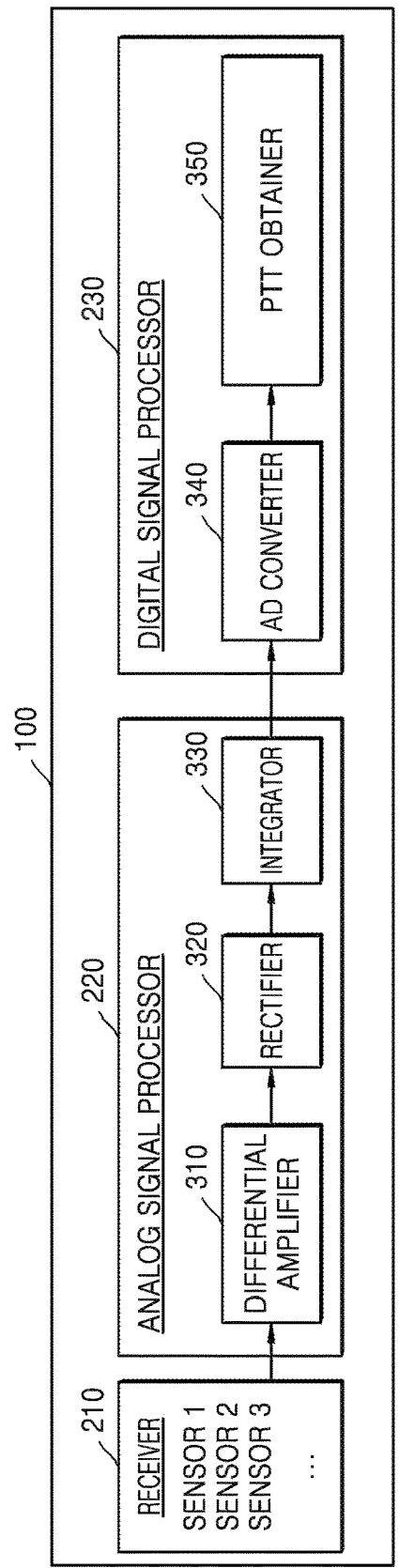
FIG. 3 is a block diagram of a configuration of a pulse wave measuring apparatus including a rectifier according to an exemplary embodiment.

FIG. 3 is a block diagram of a configuration of a pulse wave measuring apparatus 100 including a rectifier according to an exemplary embodiment.

As illustrated in FIG. 3, the pulse wave measuring apparatus 100 includes the receiver 210, the analog signal processor 220, and the digital signal processor 230. The receiver 210 may include at least two sensors. The analog signal processor 220 may include a differential amplifier 310, a rectifier 320, and an integrator 330. The digital signal processor 230 may include an AD converter 340 and a PTT obtainer 350. However, all the illustrated elements are not essential elements. The pulse wave measuring apparatus 100 may be implemented by more or less elements than the illustrated elements.

Since the receiver 210, the analog signal processor 220, and the digital signal processor 230 illustrated in FIG. 3 correspond to the receiver 210, the analog signal processor 220, and the digital signal processor 230 illustrated in FIG. 2, repeated description thereof will not be given.

The receiver 210 according to the exemplary embodiment may include at least two sensors. That is, the receiver 210 may sense pulse wave signals at at least two points of an object.

The pulse wave measuring apparatus 100 according to the exemplary embodiment may sense pulse wave signals by at least three sensors, select two pulse wave signals that have improved SNRs, and obtain the PTT. In this case, pulse waves may be stably measured even when the pulse wave signals are deteriorated by the noise or dislocation of the sensors.

For example, the sensors may be respectively positioned at at least two points apart from the heart by a first distance and at at least two points apart from the heart by a second distance at the end of a body. In this case, the pulse wave measuring apparatus 100 may select a pulse wave signal sensed by one of the at least two sensors disposed apart from the heart by the first distance and a pulse wave signal sensed by one of the at least two sensors disposed apart from the heart by the second distance. Thereafter, the pulse wave measuring apparatus 100 may obtain the PTT between the two points.

The pulse wave measuring apparatus 100 according to another exemplary embodiment senses pulse wave signals by at least three sensors, combines the sensed pulse wave signals, and may generate a pulse wave signal array. For example, the sensors may be respectively positioned at at least two points apart from the heart by the first distance and at at least two points apart from the heart by the second distance at the end of the body. In this case, the pulse wave measuring apparatus 100 selects a pulse wave signal sensed by one of the at least two sensors separated from the heart by the first distance and a pulse wave signal sensed by one of the at least two sensors disposed apart from the heart by the second distance and may obtain the PTT between the two points. The pulse wave measuring apparatus 100 combines the pulse wave signal sensed by the at least two sensors disposed apart from the heart by the first distance and the pulse wave signal sensed by the at least two sensors disposed apart from the heart by the second distance and may obtain respective PTTs. The pulse wave measuring apparatus 100 may generate the pulse wave signal array from the PTTs obtained from the combination of the pulse wave signals sensed at the plurality of points. The generated pulse wave signal array may be used for grasping the cardiovascular system characteristics.

The analog signal processor 220 according to the exemplary embodiment may include the rectifier 320 for rectifying a signal of an amplified voltage difference. The differential amplifier 310 amplifies the voltage difference between the two pulse wave signals. An output of the differential amplifier 310 may be in the form of a biphasic signal. When an integration value of one period of the output of the differential amplifier 310 is 0, it may be difficult to measure the PTT. Therefore, the rectifier 320 converts the biphasic signal into a monophasic signal so that the PTT may be correctly measured.

For example, the rectifier 320 may perform full-wave rectification on the signal of the amplified voltage difference. In another example, the rectifier 320 may perform half-wave rectification on the signal of the amplified voltage difference.

The integrator 330 according to the exemplary embodiment may be reset at every uniform point of time. The integrator 330 according to the exemplary embodiment may be reset at a point of time determined by using one of the pulse wave signals sensed by the digital signal processor 230.

For example, the integrator 330 may be reset at every point of time corresponding to a point of time at which a peak of one of the sensed pulse wave signals is detected. For example, when a cardiac cycle is 1 second, a peak generation time interval is the same as the cardiac cycle and predetermined time may be determined as 250 ms. In this case, the integrator 330 may be reset at every point of time with a lapse of 250 ms from the point of time at which the peak of one of the sensed pulse wave signals is detected.

The AD converter 340 according to the exemplary embodiment receives the result of the integrating from the analog signal processor 220 and converts the received result of the integrating into a digital signal.

The PTT obtainer 350 according to the exemplary embodiment may obtain the PTT by using the result of converting the result of the integrating into the digital signal. The PTT may be proportional to the output voltage of the integrator 330.

The digital signal processor 230 may monitor the received pulse wave signals at a predetermined sampling frequency in order to determine the point of time at which the result of the integrating is received from the analog signal processor 220 and the received result of the integrating is converted into the digital signal and the point of time at which the integrator 330 is reset. In addition, the digital signal processor 230 may monitor pre-processed pulse wave signals at the predetermined sampling frequency in order to determine the point of time at which the result of the integrating is received from the analog signal processor 220 and the received result of the integrating is converted into the digital signal and the point of time at which the integrator 330 is reset. The predetermined sampling frequency may be determined to be larger than a heart rate. For example, the predetermined sampling frequency may be determined as a value between about 100 Hz and about 500 Hz.

Figure 4A:
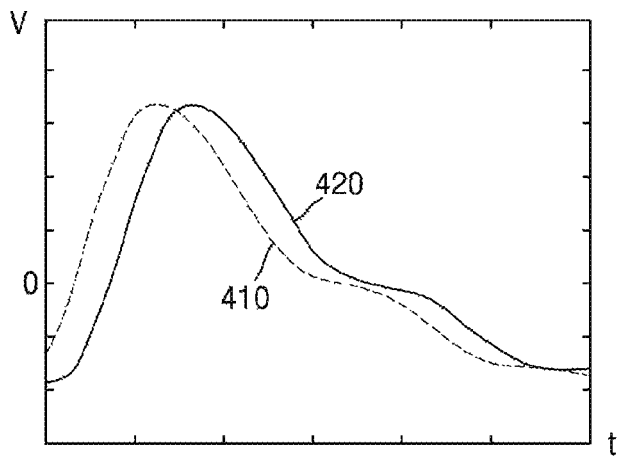
FIGS. 4A, 4B, and 4C are exemplary views of signal processing processes performed by the pulse wave measuring apparatus of FIG. 3.
Figure 4B:
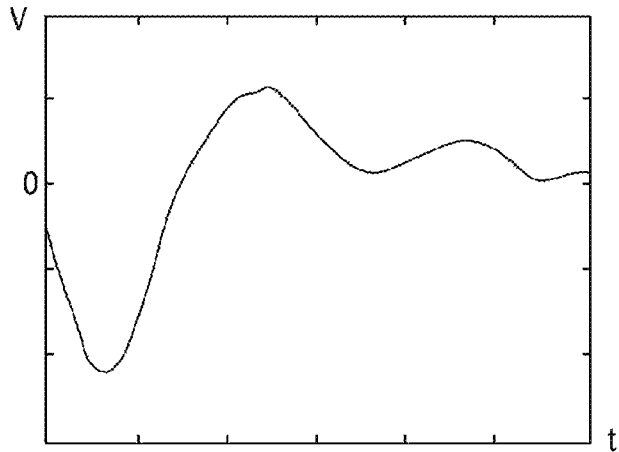
Figure 4C:
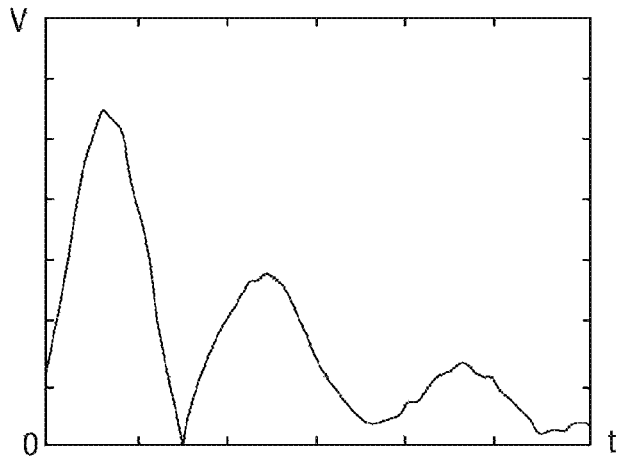

FIGS. 4A, 4B, and 4C are exemplary views of signal processing processes performed by the pulse wave measuring apparatus of FIG. 3.

FIG. 4A illustrates a result of performing pre-processing on two received pulse wave signals, for example, a result of performing noise filtering on pulse wave signals sensed at two points of an object and improving SNRs of the pulse wave signals.

FIG. 4B illustrates a result of differentially amplifying the two pulse wave signals. Referring to FIG. 4B, the result of differentially amplifying the two pulse wave signals is in the form of a biphasic signal. That is, a differential amplification signal has a negative value at a point of time at which a first pulse wave signal 410 is larger than a second pulse wave signal 420 and has a positive value at a point of time at which the first pulse wave signal 410 is smaller than the second pulse wave signal 420.

FIG. 4C illustrates a result of full-wave rectification on the differential amplification signal of FIG. 4B. That is, the full-wave rectified differential amplification signal is in the form of the biphasic signal.

The result of differentially amplifying the two pulse wave signals may be in the form of the biphasic signal. Therefore, when an integration value of one period is 0, it may be difficult to measure the PTT. The rectifier 320 converts the biphasic signal into a monophasic signal and may improve accuracy of measuring the PTT.

Figure 5:
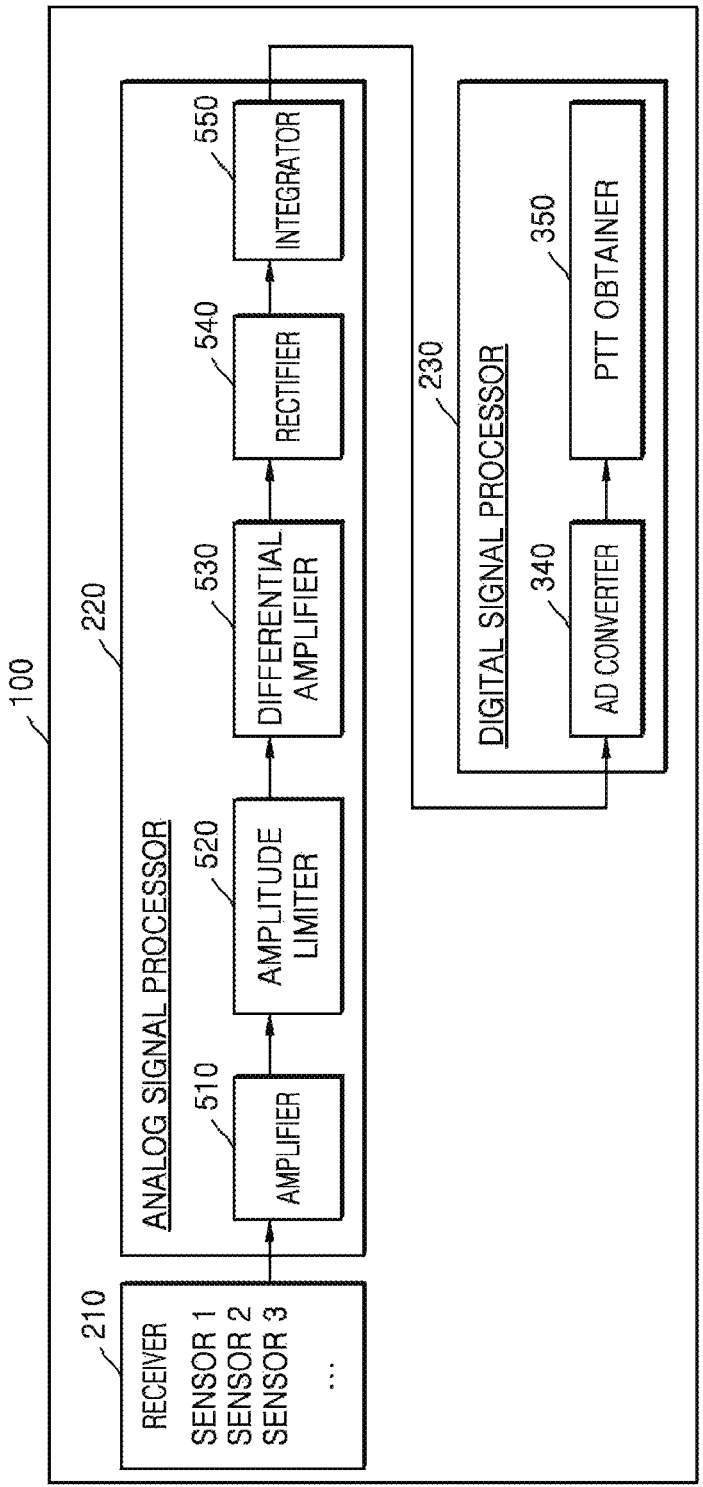
FIG. 5 is a block diagram of a configuration of a pulse wave measuring apparatus including an amplifier and an amplitude limiter according to an exemplary embodiment.

FIG. 5 is a block diagram of a configuration of a pulse wave measuring apparatus 100 including an amplifier and an amplitude limiter according to an exemplary embodiment.

As illustrated in FIG. 5, the pulse wave measuring apparatus 100 according to the exemplary embodiment includes the receiver 210, the analog signal processor 220, and the digital signal processor 230. Since the receiver 210, the analog signal processor 220, and the digital signal processor 230 illustrated in FIG. 5 correspond to the receiver 210, the analog signal processor 220, and the digital signal processor 230 illustrated in FIGS. 2 and 3, repeated description thereof will not be given.

The analog signal processor 220 according to the exemplary embodiment may include an amplifier 510, an amplitude limiter 520, a differential amplifier 530, a rectifier 540, and an integrator 550. Since the differential amplifier 530, the rectifier 540, and the integrator 550 illustrated in FIG. 5 correspond to the differential amplifier 310, the rectifier 320, and the integrator 330 illustrated in FIG. 5, repeated description thereof will not be given.

An amplitude difference may exist between pulse wave signals sensed at two points because a difference in characteristic between a sensor and a body surface exists between the respective signal measuring positions or the characteristic between the sensor and the body surface may vary in accordance with one body signal or time. In this case, when the two signals are simply differentially amplified, a result of integrating of a differential amplification signal varies every pulse so that accuracy of measuring the PTT may deteriorate.

In order to solve the problem, the pulse wave measuring apparatus 100 according to the exemplary embodiment amplifies the respective pulse wave signals before performing differential amplification, limits amplitudes of the amplified pulse wave signals to a predetermined value, and may perform differential amplification.

The amplifier 510 according to the exemplary embodiment may amplify the respective received pulse wave signals. When pre-processing is performed in order to improve SNRs of the received pulse wave signals, the amplifier 510 may amplify the respective pre-processed signals. The amplifier 510 according to the exemplary embodiment amplifies the respective pulse wave signals and may increase slopes of the pulse wave signals.

The amplitude limiter 520 according to the exemplary embodiment may limit the amplitudes of the amplified pulse wave signals to the predetermined value when the amplified pulse wave signals have values of no less than a predetermined value.

When the pulse wave signals are amplified and the amplitudes are limited to the predetermined value, a remaining section excluding a rising edge and a falling edge has a uniform value. Therefore, the signals whose amplitudes are limited have similar forms to digital pulses.

According to another exemplary embodiment, although the analog signal processor 220 does not include the amplitude limiter, the amplitudes may be limited by a saturation voltage of an amplifier. Therefore, the amplitudes may be limited only by the amplifier.

FIGS. 6A to 6F are exemplary views of signal processing processes performed by the pulse wave measuring apparatus of FIG. 5.

Figure 6A:
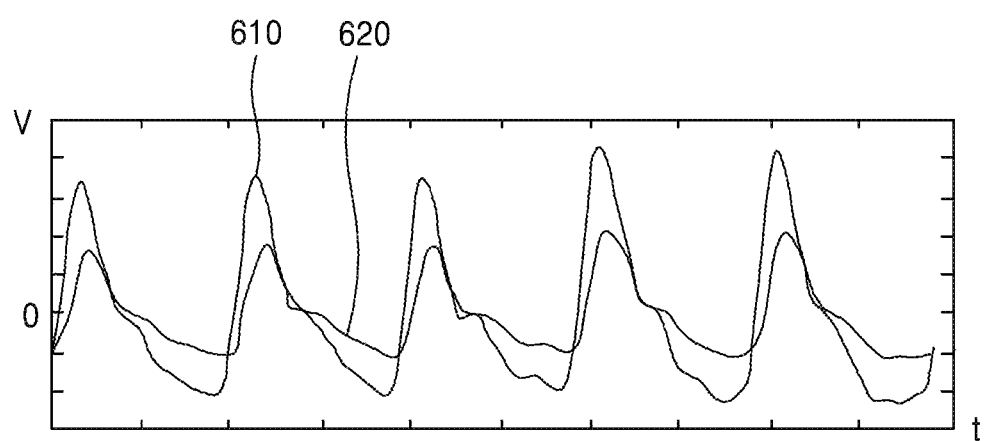
FIGS. 6A to 6F are exemplary views of signal processing processes performed by the pulse wave measuring apparatus of FIG. 5.

FIG. 6A illustrates a result of performing pre-processing on two received pulse wave signals, for example, a result of performing noise filtering on pulse wave signals sensed at two points of an object and improving SNRs of the pulse wave signals.

Figure 6B:
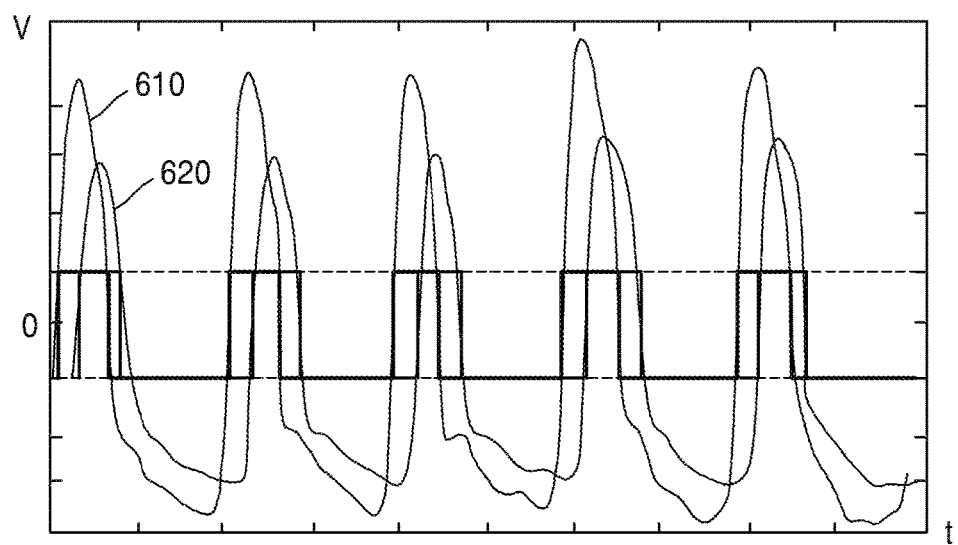

FIG. 6B is an exemplary view illustrating a process of amplifying the two signals 610 and 620 of FIG. 6A and limiting amplitudes of the two signals 610 and 620. When the two signals 610 and 620 of FIG. 6A are amplified, the slopes of the two signals 610 and 620 become steeper. The amplitude limiter 520 according to the exemplary embodiment may limit the amplitudes of the amplified pulse wave signals to the predetermined value when the amplified pulse wave signals have values of no less than a predetermined value. When the two signals 610 and 620 are amplified and the amplitudes are limited to the predetermined value, a remaining section excluding a rising edge and a falling edge has a uniform value. Therefore, the signals whose amplitudes are limited may have similar forms to digital pulses.

Figure 6C:
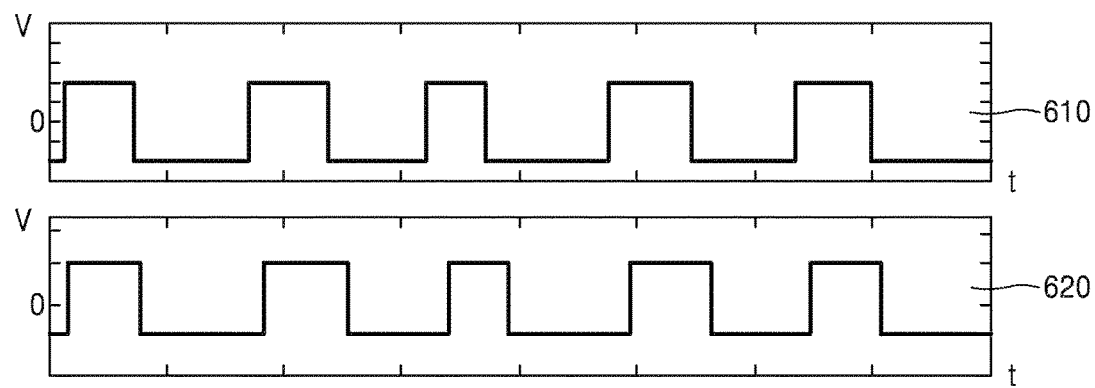

FIG. 6C illustrates a result of amplifying the two signals 610 and 620 of FIG. 6A and limiting the amplitudes of the two signals 610 and 620. A graph at an upper end of FIG. 6C illustrates a result of performing noise filtering, amplification, and amplitude limitation on the signal 610 corresponding to a pulse wave signal sensed at a point closer to the heart between the two signals 610 and 620. A graph at a lower end of FIG. 6C illustrates a result of performing noise filtering, amplification, and amplitude limitation on the signal 620 corresponding to a pulse wave signal sensed at a point remoter from the heart between the two signals 610 and 620.

Figure 6D:
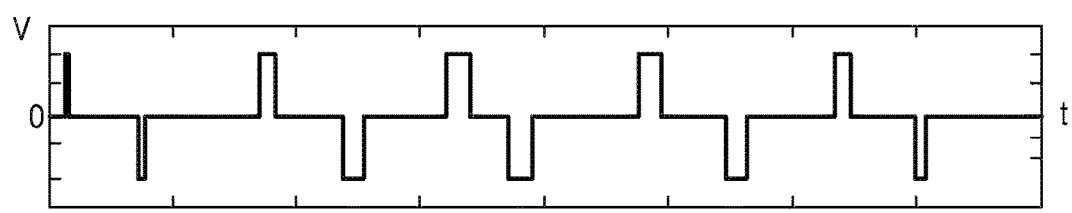

FIG. 6D illustrates a result of differentially amplifying the two signals whose amplitudes are limited. Referring to FIG. 6D, the result of differentially amplifying the two signals whose amplitudes are limited are in the form of a biphasic signal. That is, a differential amplification signal has a negative value at a point of time at which a first pulse wave signal 410 is larger than a second pulse wave signal 420 and has a positive value at a point of time at which the first pulse wave signal 410 is smaller than the second pulse wave signal 420. As such, the voltage difference between the two signals 410 and 420 are amplified but any voltage common to the two signals 410 and 420 is suppressed.

Figure 6E:
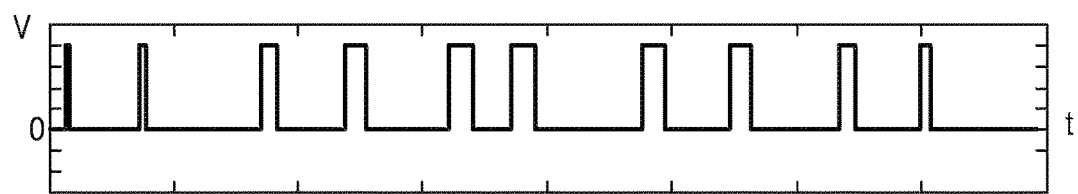

FIG. 6E illustrates a result of full-wave rectifying the differential amplification signal of FIG. 6D. That is, the full-wave rectified differential amplification signal is in the form of a monophasic signal.

Figure 6F:
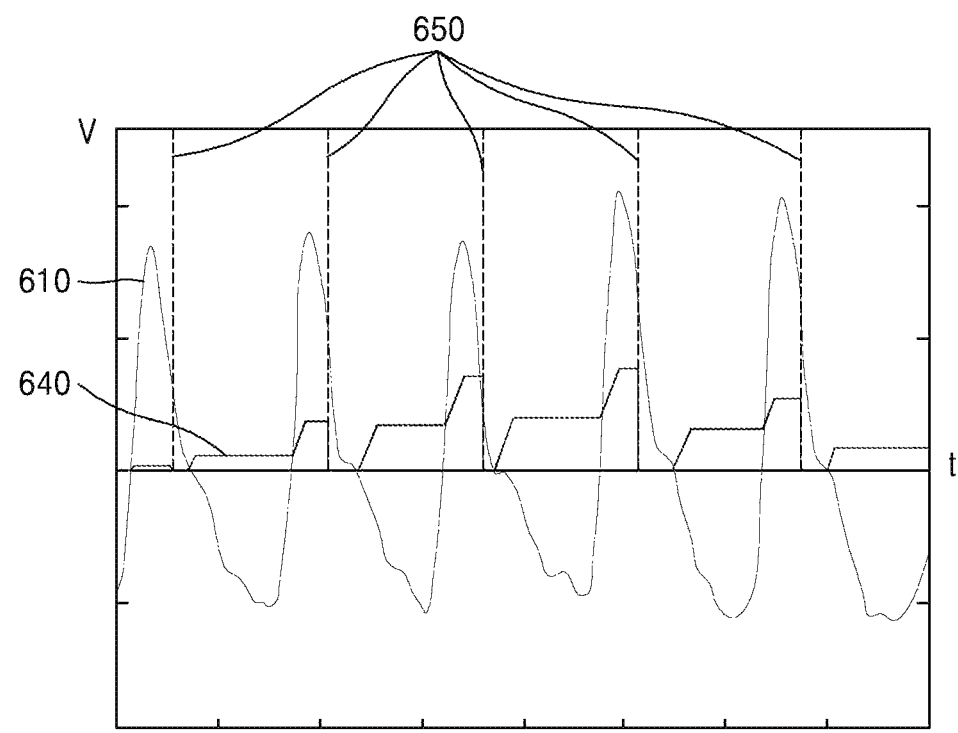

FIG. 6F is an exemplary view illustrating that the full-wave rectified signal of FIG. 6D is integrated by the integrator 550. The pulse wave measuring apparatus 100 according to the exemplary embodiment may reset the integrator 550 at every point of time 650 with a lapse of predetermined time from a point of time at which a peak of one 610 of the two pre-processed signals is detected. A result of integrating 640 is proportional to a transit time difference between the two signals 610 and 620. Therefore, the pulse wave measuring apparatus 100 may obtain the PTT by using the result of the integrating 640.

Figure 7:
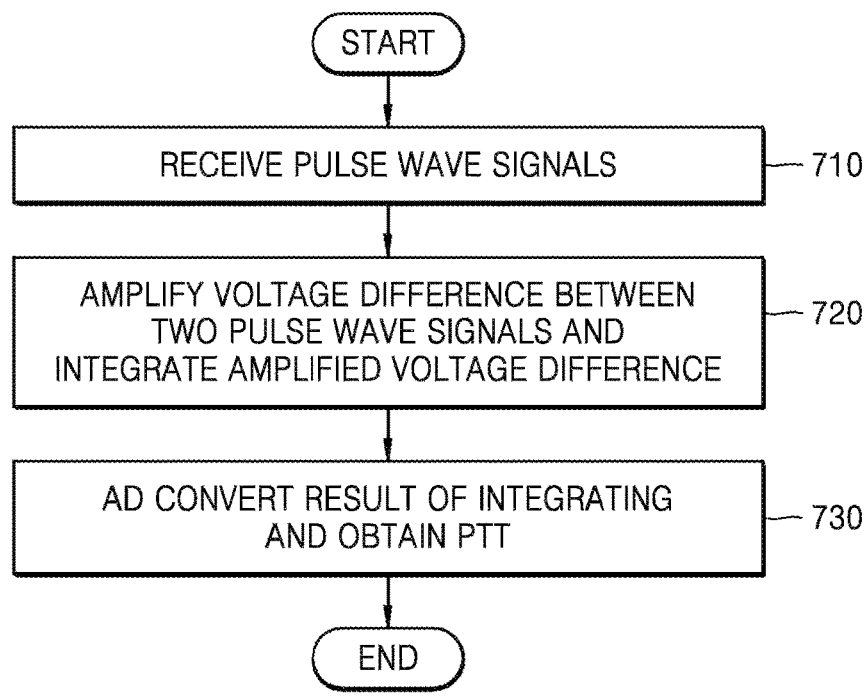
FIG. 7 is a flowchart of a pulse wave measuring method according to an exemplary embodiment.

FIG. 7 is a flowchart of a pulse wave measuring method according to an exemplary embodiment.

In operation 710, the pulse wave measuring apparatus 100 receives pulse wave signals sensed at least two points of an object.

The pulse wave measuring apparatus 100 according to the exemplary embodiment may perform pre-processing in order to improve accuracy of measuring pulse waves with respect to the received pulse wave signals. For example, the pulse wave measuring apparatus 100 may perform noise filtering in order to improve SNRs of the received pulse wave signals. In another example, the pulse wave measuring apparatus 100 may perform amplification for facilitating a subsequent signal processing process when magnitudes of the received pulse wave signals are small.

The pulse wave measuring apparatus 100 according to the exemplary embodiment may determine a point of time at which a result of integrating is AD converted by using one of the sensed pulse wave signals. In addition, the pulse wave measuring apparatus 100 may determine a point of time at which the result of the integrating is reset by using one of the sensed pulse wave signals. For example, the pulse wave measuring apparatus 100 may detect a peak of one of the received pulse wave signals.

In operation 720, the pulse wave measuring apparatus 100 amplifies a voltage difference between two pulse wave signals among the received pulse wave signals and integrates the amplified voltage difference.

The pulse wave measuring apparatus 100 according to the exemplary embodiment may further include a process of rectifying a signal of the amplified voltage difference. For example, the pulse wave measuring apparatus 100 may perform full-wave rectification on the signal of the amplified voltage difference. In another example, the pulse wave measuring apparatus 100 may perform half-wave rectification on the signal of the amplified voltage difference.

In operation 730, the pulse wave measuring apparatus 100 AD converts the result of the integrating and obtains the PTT between the two points corresponding to the two pulse wave signals.

The pulse wave measuring apparatus 100 according to the exemplary embodiment AD converts the result of the integrating at every uniform time and may obtain the PTT. Here, the uniform time may include, for example, a point of time corresponding to a point of time at which a peak of one of the received pulse wave signals is detected. In another example, the uniform time may be determined as a point of time corresponding to a point of time at which a valley of one of the received pulse wave signals is detected. In another example, the uniform time may be determined as a point of time corresponding to a point of time at which a magnitude of one of the received pulse wave signals is 0 V.

The pulse wave measuring apparatus 100 may use the obtained PTT for analyzing the cardiovascular system characteristics. For example, the obtained PTT may be used for estimating blood pressure, elasticity of a blood vessel, and an age of a blood vessel.

FIG. 8 is a flowchart of a pulse wave measuring method according to another exemplary embodiment.

In operation 810, the pulse wave measuring apparatus 100 may receive pulse wave signals sensed at least two points of an object.

The pulse wave measuring apparatus 100 according to the exemplary embodiment may emit light to an object. The pulse wave measuring apparatus 100 may receive at least one of emitted light that passes through the object and emitted light that is reflected from the object. The pulse wave measuring apparatus 100 photoelectric converts the received light and may generate the pulse wave signals.

The pulse wave measuring apparatus 100 according to the exemplary embodiment may perform pre-processing in order to improve accuracy of measuring pulse waves with respect to the received pulse wave signals. For example, the pulse wave measuring apparatus 100 may perform noise filtering in order to improve SNRs of the received pulse wave signals. In another example, the pulse wave measuring apparatus 100 may perform amplification for facilitating a subsequent signal processing process when magnitudes of the received pulse wave signals are small.

In operation 820, the pulse wave measuring apparatus 100 may amplify the respective received pulse wave signals.

The higher amplification rates of the pulse wave signals, the steeper slopes of the pulse wave signals.

When pre-processing is performed on the received light according to the exemplary embodiment, the pulse wave measuring apparatus 100 may amplify the respective pre-processed signals.

In operation 830, the pulse wave measuring apparatus 100 may limit amplitudes of the respective amplified pulse wave signals.

The pulse wave measuring apparatus 100 may limit the amplitudes of the amplified pulse wave signals to the predetermined value when the amplified pulse wave signals have values of no less than a predetermined value. For example, the pulse wave measuring apparatus 100 may limit the amplitudes of the amplified signals to uniform values by using an amplitude limiter. In another example, when the pulse wave measuring apparatus 100 does not include the amplitude limiter, the amplitudes of the amplified pulse wave signals may be limited by a saturation voltage of an amplifier.

When the pulse wave signals are amplified and the amplitudes are limited to the predetermined value, a remaining section excluding a rising edge and a falling edge has a uniform value. Therefore, it is possible to improve accuracy of measuring the PTT.

In operation 840, the pulse wave measuring apparatus 100 may amplify a voltage difference between the two signals whose amplitudes are limited.

The pulse wave measuring apparatus 100 according to the exemplary embodiment may amplify the voltage difference between the two signals by using a differential amplifier. The voltage difference between the two signals may represent a phase difference between the two signals. Therefore, the PTT may be obtained by using the voltage difference between the two signals.

In operation 850, the pulse wave measuring apparatus 100 may rectify a signal of the amplified voltage difference.

The pulse wave measuring apparatus 100 according to the exemplary embodiment may perform half-wave rectification or full-wave rectification so that the signal of the amplified voltage difference is in the form of a monophasic signal.

In operation 860, the pulse wave measuring apparatus 100 may integrate the rectified signal.

At this time, the result of the integrating is proportional to the PTT between the two points.

The pulse wave measuring apparatus 100 according to the exemplary embodiment may reset the result of the integrating at every predetermined point of time. For example, a period of resetting the result of the integrating may correspond to a cardiac cycle.

In operation 870, the pulse wave measuring apparatus 100 may AD converts the result of the integrating.

The pulse wave measuring apparatus 100 according to the exemplary embodiment may AD converts the result of the integrating at every predetermined point of time. For example, a period of AD converting the result of the integrating may correspond to the cardiac cycle.

In operation 880, the pulse wave measuring apparatus 100 may obtain the PTT between the two points corresponding to the two pulse wave signals by using the digitalized result of the integrating.

The pulse wave measuring apparatus 100 according to the current exemplary embodiment performs an analog signal processing process on the sensed pulse wave signals and may correctly measure pulse waves without a high speed sampling frequency. Therefore, the pulse wave measuring apparatus 100 according to the current exemplary embodiment may be used for a mobile health management system by reducing required computing power, an operation amount, and a memory capacity. In addition, since the pulse wave measuring apparatus 100 according to the current exemplary embodiment may obtain the PTT by measuring the pulse waves at the two close points by a low system specification, the pulse wave measuring apparatus 100 may be used for a wearable apparatus.

The pulse wave measuring apparatus 100 according to the current exemplary embodiments may include a user interface apparatus such as a processor, a memory for storing and executing program data, a permanent storage such as a disk drive, a communication port that communicates with an external apparatus, a touch panel, a key, and a button. Methods implemented by a software module or algorithm may be stored in a computer readable recording medium as computer readable codes or program commands that may be executed on the processor. Here, the computer readable recording medium may be a magnetic storage medium (for example, a read-only memory (ROM), a random-access memory (RAM), a floppy disk, or a hard disk) or an optical reading medium (for example, a CD-ROM or a digital versatile disc (DVD)). The computer readable recording medium is dispersed to computer systems connected by a network so that the computer readable codes may be stored and executed by a dispersion method. The recording medium is computer readable, is stored in a memory, and may be executed by the processor.

The current exemplary embodiment may be represented by function block configurations and various processing processes. The function blocks may be implemented by various numbers of hardware or/and software configurations that execute specific functions. For example, the current exemplary embodiment may adopt direct circuit configurations such as a memory, processing, logic, and a look-up table that may execute various functions by control of one or more microprocessors or other controlling apparatuses. Like that elements may be executed by software programming or software elements, the current exemplary embodiment may be implemented by programming or scripting languages such as C, C++, Java, and assembler including various algorithms implemented by a data structure, processes, routines or a combination of other programming configurations. Functional aspects may be implemented by algorithm executed by one or more processors. In addition, the current exemplary embodiment may adopt a conventional art in order to set an electronic environment, process a signal, and/or process data. The terms such as "mechanism", "element", "unit", and "configuration" may be widely used and are not limited to mechanical and physical configurations. The terms may include meaning of a series of routines of software in association with the processor.

The specific executions described by the current exemplary embodiment are only exemplary and do not limit the scope of the inventive concept. In order to simplify the specification, description of conventional electronic configurations, control systems, software, and other functional aspects of the systems may not be given. In addition, connection of lines or connecting members among the elements in the drawings exemplarily illustrate functional connections and/or physical or circuit connections and may be replaced or represented as additional various functional connections, physical connections, or circuit connections in a real apparatus.

The foregoing exemplary embodiments are merely exemplary and are not to be construed as limiting. The present disclosure can be readily applied to other types of apparatuses. Unless an order of the processes that form the method is clearly described, the processes may be performed in an appropriate order. Also, the description of the exemplary embodiments is intended to be illustrative, and not to limit the scope of the claims, and many alternatives, modifications, and variations will be apparent to those skilled in the art.

What is claimed is:

1. A pulse wave measuring apparatus comprising:
   a receiver configured to receive pulse wave signals sensed at at least two points of an object, the receiver comprising at least two sensors configured to sense the pulse wave signals, respectively;
   an analog signal processor configured to amplify a voltage difference between two pulse wave signals from among the received pulse wave signals and integrate the amplified voltage difference; and
   a digital signal processor configured to analog to digital (AD) convert a value of the integrated amplified voltage difference and obtain, from the converted value, a pulse transit time (PTT) between the at least two points corresponding to the two pulse wave signals,
   wherein the digital signal processor is configured to output the obtained PTT,
   wherein the receiver comprises a first sensor configured to sense a first pulse wave signal at a first point and a second sensor configured to sense a second pulse wave signal at a second point, the first point having a first distance from a heart of the object and the second point having a second distance from the heart of the object, the first distance and the second distance being different from each other,
   wherein the analog signal processor comprises a rectifier configured to rectify a signal of the amplified voltage difference.

2. The pulse wave measuring apparatus of claim 1, wherein the analog signal processor comprises:
   a differential amplifier configured to amplify the voltage difference between the two pulse wave signals; and
   an integrator configured to integrate the signal of the amplified voltage difference.

3. The pulse wave measuring apparatus of claim 2, wherein the digital signal processor is further configured to determine a point of time at which a result output from the integrator is reset by using one of the sensed pulse wave signals, and
   wherein the result output from the integrator is reset at every determined point of time.

4. The pulse wave measuring apparatus of claim 1, wherein the rectifier is further configured to perform full-wave rectification on the signal of the amplified voltage difference.

5. The pulse wave measuring apparatus of claim 1, wherein the rectifier is further configured to perform half-wave rectification on the signal of the amplified voltage difference.

6. The pulse wave measuring apparatus of claim 1, wherein the analog signal processor further comprises an amplifier configured to amplify the received pulse wave signals.

7. The pulse wave measuring apparatus of claim 6, wherein the analog signal processor further comprises an amplitude limiter configured to limit amplitudes of the amplified pulse wave signals to a predetermined value in response to the amplitudes of the amplified pulse wave signals being equal to or greater than the predetermined value.

8. The pulse wave measuring apparatus of claim 1, wherein the digital signal processor is further configured to determine a point of time at which the integrated amplified voltage difference is to be AD converted by using one of the sensed pulse wave signals, AD convert the integrated amplified voltage difference at every determined point of time, and obtain the PTT.

9. The pulse wave measuring apparatus of claim 1, wherein the digital signal processor is further configured to detect a peak of one of the sensed pulse wave signals, AD convert the integrated amplified voltage difference at every determined point of time corresponding to a point of time at which the peak is detected, and obtain the PTT.

10. The pulse wave measuring apparatus of claim 1, further comprising a light emitter configured to emit light to the object,
wherein the receiver is further configured to receive at least one of the light that is emitted from the light emitter and pass through the object and the light that is emitted from the light emitter and reflected from the object, photoelectrically convert the received light, and generate the pulse wave signals.

11. A pulse wave measuring method performed by a pulse wave measuring apparatus, the pulse wave measuring method comprising:
receiving, by a receiver of the pulse wave measuring apparatus, pulse wave signals sensed at at least two points of an object, the receiver comprising at least two sensors configured to sense the pulse wave signals, respectively;
amplifying, by an analog signal processor of the pulse wave measuring apparatus, a voltage difference between two pulse wave signals from among the received pulse wave signals;
rectifying, by a rectifier of the pulse wave measuring apparatus, a signal of the amplified voltage difference;
integrating, by the analog signal processor of the pulse wave measuring apparatus, the rectified signal of the amplified voltage difference;
analog-to-digital (AD) converting, by a digital signal processor of the pulse wave measuring apparatus, a value of the integrated amplified voltage difference;
obtaining, by the digital signal processor of the pulse wave measuring apparatus, from the converted value, a pulse transit time (PTT) between the at least two points corresponding to the two pulse wave signals and outputting the obtained PTT,
wherein the receiver comprises a first sensor configured to sense a first pulse wave signal at a first point and a second sensor configured to sense a second pulse wave signal at a second point, the first point having a first distance from a heart of the object and the second point having a second distance from the heart of the object, the first distance and the second distance being different from each other.

12. The pulse wave measuring method of claim 11, wherein the rectifying the signal of the amplified voltage difference comprises performing full-wave rectification on the signal of the amplified voltage difference.

13. The pulse wave measuring method of claim 11, wherein the rectifying the signal of the amplified voltage difference comprises performing half-wave rectification on the signal of the amplified voltage difference.

14. The pulse wave measuring method of claim 11, wherein the receiving the pulse wave signals comprises amplifying the received pulse wave signals.

15. The pulse wave measuring method of claim 14, wherein the amplifying the received pulse wave signals comprises limiting amplitudes of the amplified pulse wave signals to a predetermined value in response to the amplitudes of the amplified pulse wave signals being equal to or greater than the predetermined value.

16. The pulse wave measuring method of claim 11, further comprising determining, by the digital signal processor of the pulse wave measuring apparatus, a point of time at which the value of the integrated amplified voltage difference is to be AD converted by using one of the sensed pulse wave signals,
wherein the obtaining the PTT comprises AD converting the value of the integrated amplified voltage difference corresponding to every determined point of time.

17. The pulse wave measuring method of claim 11, further comprising determining, by the digital signal processor of the pulse wave measuring apparatus, a point of time at which the value of the integrated amplified voltage difference is reset by using one of the sensed pulse wave signals,
wherein the integrating the amplified voltage difference comprises resetting the value of the integrated amplified voltage difference at every determined point of time.

18. The pulse wave measuring method of claim 11, further comprising:
emitting light to the object;
receiving at least one of the light that is emitted and passes through the object and the light that is emitted and reflected from the object;
photoelectrically converting the received light; and
generating the pulse wave signals from the photoelectrically converted light.

* * * * *